US007939785B2

(12) United States Patent
Collins, Sr. et al.

(10) Patent No.: US 7,939,785 B2
(45) Date of Patent: May 10, 2011

(54) MICROWAVE-ASSISTED CHROMATOGRAPHY PREPARATION

(75) Inventors: Michael Collins, Sr., Charlotte, NC (US); Wyatt P. Hargett, Jr., Matthews, NC (US); James Edward Thomas, Harrisburg, NC (US); E. Keller Barnhardt, Charlotte, NC (US); Michael Collins, Jr., Charlotte, NC (US)

(73) Assignee: CEM Corporation, Matthews, NC (US)

( * ) Notice: Subject to any disclaimer, the term of this patent is extended or adjusted under 35 U.S.C. 154(b) by 352 days.

(21) Appl. No.: 12/020,711

(22) Filed: Jan. 28, 2008

(65) Prior Publication Data
US 2008/0116363 A1    May 22, 2008

Related U.S. Application Data

(62) Division of application No. 10/923,243, filed on Aug. 20, 2004, now Pat. No. 7,348,526.

(51) Int. Cl.
*H05B 6/64* (2006.01)
(52) U.S. Cl. ........................... 219/679; 219/678
(58) Field of Classification Search .................. 219/676, 219/678, 679
See application file for complete search history.

(56) References Cited

U.S. PATENT DOCUMENTS

| | | |
|---|---|---|
| 3,894,815 A | 7/1975 | Beeton |
| 3,937,034 A | 2/1976 | Eskeli |
| 4,330,946 A | 5/1982 | Tillitt et al. |
| 4,936,112 A | 6/1990 | Miller |
| 5,332,872 A | 7/1994 | Ewanek |
| 5,356,277 A | 10/1994 | Yamaguchi et al. |
| 5,447,077 A | 9/1995 | Lautenschlager |
| 5,584,675 A | 12/1996 | Steurer et al. |
| 5,722,816 A | 3/1998 | Shimada et al. |
| 5,749,416 A | 5/1998 | Belcher |
| 6,029,498 A | 2/2000 | Walters et al. |

(Continued)

FOREIGN PATENT DOCUMENTS

JP    2003-511358 A    3/2003

(Continued)

OTHER PUBLICATIONS

Dorf, The Electrical Engineering Handbook, Second Ed., (1997), CRC Press LLC, USA.

(Continued)

*Primary Examiner* — Daniel Robinson
(74) *Attorney, Agent, or Firm* — Summa, Additon & Ashe, P.A.

(57) ABSTRACT

An instrument and associated method are disclosed for preparing samples for column chromatography. The method includes the steps of applying microwave energy to a sample composition containing at least one solvent to encourage a chemical reaction and generate desired products, thereafter mixing an absorbent media with the sample to absorb the solvent, the media being compatible with liquid chromatography that will separate the expected products, being chemically inert to the expected products, and being added in an amount sufficient to provide a substantially dry mixture of the media and the sample, but less than an amount that overly broadens the resolution of the sample during liquid chromatography, thereafter applying microwave energy to the dry mixture of the media and the sample to thereby encourage the solvent to evaporate under the influence of the microwave energy, and thereafter adding the dry mixture of the media and the remaining sample to a liquid chromatography column and separating the components of the remaining sample for identification and purification purposes.

21 Claims, 6 Drawing Sheets

U.S. PATENT DOCUMENTS

| | | | |
|---|---|---|---|
| 6,084,226 | A | 7/2000 | Greene et al. |
| 6,139,733 | A | 10/2000 | Hargro et al. |
| 6,258,329 | B1 | 7/2001 | Mutterer, Jr. et al. |
| 6,273,691 | B1 | 8/2001 | Morimoto et al. |
| 6,530,760 | B1 | 3/2003 | Graber et al. |
| 6,630,354 | B2 | 10/2003 | Stone |
| 6,649,051 | B1 | 11/2003 | Jamalabadi et al. |
| 6,744,024 | B1 | 6/2004 | Hayes et al. |
| 6,753,517 | B2 | 6/2004 | Jennings |
| 6,858,434 | B1 | 2/2005 | Williams |
| 6,865,926 | B2 | 3/2005 | O'Brien et al. |
| 6,917,023 | B2 | 7/2005 | Hayes et al. |
| 6,952,945 | B2 | 10/2005 | O'Brien et al. |
| 7,348,526 | B2 * | 3/2008 | Collins et al. .............. 219/679 |
| 2002/0104801 | A1 | 8/2002 | Voute et al. |
| 2003/0015019 | A1 | 1/2003 | O'Brien |
| 2003/0170149 | A1 | 9/2003 | Jennings et al. |
| 2003/0203502 | A1 | 10/2003 | Zenhausern et al. |
| 2003/0205455 | A1 | 11/2003 | Jamalabadi et al. |
| 2003/0205456 | A1 | 11/2003 | Jamalabadi et al. |
| 2003/0217973 | A1 | 11/2003 | Horsman et al. |
| 2004/0020923 | A1 | 2/2004 | Collina et al. |

FOREIGN PATENT DOCUMENTS

| | | |
|---|---|---|
| WO | WO 00/23861 A | 4/2000 |
| WO | WO 2004/058379 A1 | 7/2004 |

OTHER PUBLICATIONS

Hawley's Condensed Chemical Dictionary, Twelfth Edition (1993), Van Nostrand Reinhold.

Stratospheres™ Synthesis and Purification Guide; Published by Polymer Laboratories; www.polymerlabs.com/stratospheres, Dec. 10, 2004.

Organic Synthesis and Purification Catalog (2003-2004); Published by Silicycle™.

About the Explorer System; www.cemsynthesis.com/html/exp_page.htm, Dec. 10, 2004.

About the Navigator System; www.cemsynthesis.com/html/nav_page.htm, Dec. 10, 2004.

Meet Voyager; www.cemsynthesis.com/html/voy_page.htm, Dec. 10, 2004.

Maichin B, et al., "Investigation of microwave assisted drying of samples and evaporation of aqueous solutions in trace element anaylsis," Fresenius' Journal of Analytical Chemistry, vol. No. 366, No. 1, Jan. 2000, pp. 26-29, Anton Paar GmbH, Graz, Austria.

Mason, C., "The Evolution of Microwave Technology for Synthetic Chemistry," CEM Microwave Technology Ltd., Jun. 23, 2004, pp. 1-84, retrieved from the internet: www.chemsourcesymposia.org.uk/registered/speakers%20presentations/symposium%201%205%20mason.pdf> Nov. 15, 2005.

Royal Society of Chemistry, "ChemSource 2004," retrieved from the internet: www.rsc.org/pdf/findusdiv/ind013jun04.pdf> retrieved on Nov. 15, 2005.

SMI-Labhut Ltd., "What is Flash Chromatography?" p. 1, retrieved from the internet: www.labhut.com/education/flash/index,php> Nov. 17, 2005.

SMI-Labhut Ltd., "Solid Sample Introduction Module for JumboFlash Systems," retrieved from the internet: www.labhut.com/products/flash/jumboflash/ssim/php> Nov. 16, 2005.

Chemsources 2004, retrieved from internet: www.chemsourcesymposia.org/uk/REGISTERED/> Nov. 15, 2005.

* cited by examiner

MICROWAVE-ASSISTED CHROMATOGRAPHY PREPARATION

RELATED APPLICATIONS

This is a divisional application of Ser. No. 10/923,243 filed Aug. 20, 2004 and now U.S. Pat. No. 7,348,526.

FIELD OF THE INVENTION

The present invention relates to microwave-assisted flash chromatography, and in particular relates to a microwave instrument that offers particular advantages useful for sample preparation and purification via chromatography.

BACKGROUND OF THE INVENTION

The present invention relates to devices for microwave-assisted chromatography. As generally recognized in the chemical arts, many chemical reactions can be initiated or accelerated by increasing the temperature—i.e. heating—the reactants. Accordingly, carrying out chemical reactions at elevated (i.e., above ambient) temperatures is a normal part of many chemical processes.

The benefit of using controlled microwave energy for elevating the temperature of a chemical reaction is well known. For example, U.S. Pat. No. 6,753,517 to Jennings, incorporated entirely herein by reference, discloses a microwave-assisted chemical synthesis instrument using tightly controlled microwave energy.

More recently, researchers have applied microwave assisted chemistry to the technique of chromatography. Chromatography in the present context includes liquid and gas chromatography. Of the two, the instrument of the present invention primarily relates to liquid chromatography, particularly as it pertains to solvent evaporation and sample preparation for elution.

Liquid chromatography is a technique utilized in both preparative and analytical chemistry. Liquid chromatography comprises a stationary phase interacting with a mobile phase. Typically, the stationary phase is a surface-active powder such as silica, alumina, or an inert size-separating material like a gel-permeation chromatography packing, or the like. This powder is contained in a chromatographic column. In preparative chemistry, the mobile phase generally consists of a reaction solvent and a chemical to be identified, analyzed, or purified. This is collectively referred to as a sample. The mobile phase carrying the sample is caused to migrate through the stationary phase. Depending on how the sample interacts with the surface characteristics of the stationary phase, different compounds will migrate through the stationary phase at different rates. Preparative chemistry is useful for identifying and purifying various chemical components in the sample using analytical chemistry. Analytical chemistry utilizes carrier solvents to move the sample through the stationary phase.

In some instances, the reaction solvent is not ideal for the further purification of the compound dissolved therein. Residual reaction solvent in the stationary phase can result in the problem of poor separation and recovery of the desired components during elution.

One solution to this problem is to utilize a rotary evaporator. This procedure, however, is time consuming and not entirely effective. For example, the use of larger chromatography columns having more stationary phase will require one or more hours to evaporate the reaction solvent.

Another solution to this problem is to apply heat with or without vacuum. This procedure, however, may result in the degradation of the stationary phase or melting of the chromatography column material.

Another solution to the problem of residual reaction solvent in the stationary phase is to flash away the solvent using microwave energy. Microwave energy is used to vaporize liquid in U.S. Pat. No. 4,330,946 to Courneya. The Courneya '946 patent discloses microwave energy to vaporize liquid from agricultural material, such as grain. The Coumeya '946 patent further discloses the use of air inlets for introducing air to sweep across the material, aerosolize the vapor and carry it away via a vacuum pump. The Coumeya '946 patent also states the need for an auger-driven process to insure proper agitation of the material, as well as to move the material through the apparatus. A heat reclaim mechanism assists the microwave energy drying process.

As previously stated, microwave energy has been applied to the technique of chromatography. For example, U.S. Pat. No. 6,029,498 to Walters et al. discloses the incorporation of microwave absorbing material into the chromatography column itself or positions adjacent the column. The chromatography sample contained therein is heated by the microwave absorbing material via conduction or convection. The Walters '498 patent further discloses, however, the use of a heated chromatography column for the purpose of enhancing the speed of separation and the consistency of elution times.

Another example of the application of microwave energy to liquid chromatography is demonstrated in U.S. Pat. No. 6,630,354 to Stone. The Stone '354 patent discloses a method of using microwave-induced dielectric polarization to enhance the diffusivity of a liquid or a supercritical fluid mobile phase in chromatography, while having essentially no effect on other physical properties of the mobile phase. The primary focus of the Stone '354 patent, however, is to increase the diffusivity of the reaction solvent and to combine the advantages of liquid and gas chromatography. Heating the reaction solvent to increase its diffusivity could be hazardous if the solvent is combustible. To overcome this, the Stone '354 patent discloses the use of microwave pulses. The Stone '354 patent further states that a microwave apparatus capable of delivering very short pulses of radiation is not available, and instead teaches the use of a conventional, non-cycling microwave oven.

Yet another example of the application of microwave energy to liquid chromatography is demonstrated in U.S. Pat. No. 6,649,051 to Jamalabadi et al. The Jamalabadi '051 patent discloses a method of processing a sample into a flow-through device containing a porous solid media and thereafter subjecting the device to microwave energy. As in the Stone '354 patent, the Jamalabadi '051 patent discloses the use of a conventional microwave oven and further discloses the use of a more precise microwave power source, such as one manufactured by CEM Corporation of Matthews, N.C., USA, the assignee of the present invention.

Yet another example of the application of microwave energy to liquid chromatography is demonstrated in U.S. Pat. Application Publication No. 20030205456 to Jamalabadi et al. The Jamalabadi application discloses a method of processing a sample comprising introducing a sample in a flow-through device containing a porous solid media therein. The flow-through device is defined as having walls and having an inlet end and an outlet end; a solid porous media disposed within the flow-through device including attached active components. After introducing a sample into the flow-through device, the device is subjected to a radiated energy source, such as microwave energy, prior to further chromatography steps.

Furthermore, none of the above-referenced patents or applications teaches or suggests the use of a dry-loading technique. A typical dry-loading technique includes addition of a given amount of chromatography media, for example silica or alumina, to a vessel holding the sample. The sample is preferably dissolved in a reaction solvent. Following absorption of the sample by the chromatography media, the reaction solvent is evaporated and evacuated, leaving dried chromatography media containing the sample. The dried chromatography media is then dry-loaded, either manually or automatically, onto a separation chromatography column for separation and identification of the sample components.

The advantage of a dry-loading technique lies in the flexibility it allows for evaporation of the reaction solvent. Accordingly, dry-loading streamlines the subsequent separation and analysis of the sample components. The dry-loading technique is infinitely adjustable for a given sample volume, as opposed to the limitations imposed by preloading a specific amount of chromatography media into a flow-through device, or a sample module, or the like. For example, if the flow-through device contains too little chromatography media for a given amount of reaction solvent, the chromatography media will not sufficiently absorb the solvent. Subsequent heating of the chromatography media to evaporate the solvent will result in a highly viscous mixture from which the sample cannot be salvaged. If the flow-through device contains too much chromatography media for a given amount of reaction solvent, subsequent separation and identification chromatography efforts will be confounded by the excess media, resulting in wide, overlapping peaks having poor resolution.

OBJECT AND SUMMARY OF THE INVENTION

Therefore, it is an object of the invention to provide a microwave instrument suitable for microwave assisted chemistry, including accelerated chemical synthesis and sample preparation for flash chromatography and liquid chromatography. The invention meets this object with an instrument for carrying out a reaction in reaction solvents in a microwave transparent reaction vessel followed by evaporating and evacuating reaction solvents from the chromatography media. The invention further includes a source of microwave radiation and a microwave cavity in wave communication with the source for applying microwave energy to a sample. The sample includes a solid phase chromatography media and a solvent. The invention further includes a vessel for holding the sample in the microwave cavity for evaporating the solvent when microwaves are applied to the vessel, and a gas pump in gas communication with the vessel for moving gases through the vessel during the application of microwaves to the vessel to facilitate the evaporation of the reaction solvent from the chromatography media.

It is further an object of the present invention to provide a microwave assisted chromatography sample preparation instrument, including a microwave source, and a mechanism for controlling the application of microwave energy from the microwave source. The instrument further includes a vessel in wave communication with the microwave source for evaporating solvent, a gas inlet tube and a gas exit tube about the vessel for allowing the influx of make-up gas and the evacuation of solvent, respectively, and a gas pump in physical communication with the vessel to facilitate the evaporation of solvent. The gas pump, gas inlet tube, and gas exit tube create a gas flow through the evaporation vessel to evaporate the solvent from the chromatography sample during and between applications of microwave energy.

It is yet another object of the present invention to provide a method of preparing samples for column chromatography, especially flash chromatography, comprising adding a sample including reaction solvent to a solid phase chromatography medium and applying microwave energy to the sample while concurrently providing a gas flow over and around the sample. The solvent is thereby encouraged to evaporate under the influence of the microwave energy and the flowing gas.

It is yet another object of the present invention to provide a method for microwave assisted chromatography sample preparation, including mixing a sample dissolved in a reaction solvent with a solid phase chromatography medium, applying microwave energy to the sample to evaporate the solvents therein, and create a gas flow through a vessel to evacuate the vaporized solvents. The invention further provides for monitoring the temperature of the chromatography media using temperature sensors and moderating the temperature of the sample. A microprocessor is used to control the steps of applying microwave energy, moderating the temperature of the sample, and creating the gas flow. The step of creating a gas flow further includes creating a vacuum in the vessel.

It is yet another object of the present invention to provide a method of preparing samples for column chromatography, such as flash chromatography, including applying microwave energy to a sample composition containing at least one solvent to encourage a chemical reaction and generate desired products. Thereafter, the method includes mixing an absorbent media with the sample to absorb the solvent. The media is compatible with liquid chromatography that will separate the expected products, is chemically inert to the expected products, and is added in an amount sufficient to provide a substantially dry mixture of the media and the sample, but less than an amount that overly broadens the resolution of the sample during liquid chromatography. The method thereafter provides for applying microwave energy to the dry mixture of the media and the sample to thereby encourage the solvent to evaporate under the influence of the microwave energy. The method of the invention then includes adding the dry mixture of the media and the remaining sample to a liquid chromatography column and separating the components of the remaining sample for identification and purification purposes.

It is yet another object of the present invention to provide a method of preparing samples for column chromatography as described, including the addition of scavenging compositions, catalysts, and coupling reagents.

It is yet another object of the present invention to provide a method of dry-loading samples for column chromatography.

It is further an object of the invention to provide the previously discussed aspects while monitoring the temperature of the sample.

It is further an object of the invention to provide the previously discussed aspects under the electronic control of a microprocessor, and additionally providing that the microprocessor moderate the application of microwave energy based upon the monitored temperature.

The foregoing and other objects and advantages of the invention and the manner in which the same are accomplished will become clearer based on the followed detailed description taken in conjunction with the accompanying drawings in which:

DETAILED DESCRIPTION OF THE INVENTION

Figure 1:
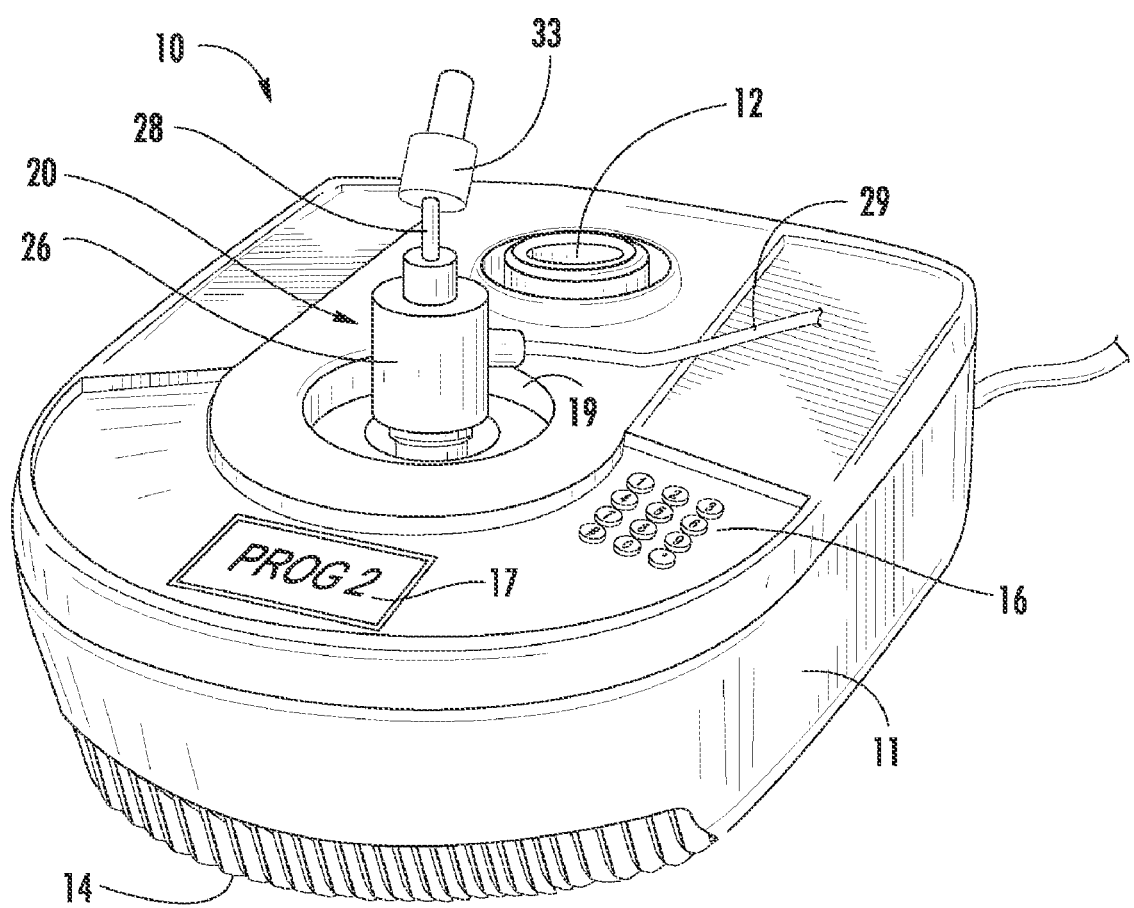
FIG. 1 is a perspective view of the invention showing the instrument with the vessel placed in the microwave cavity.

In a first embodiment, the invention is a sample preparation instrument for flash chromatography. The instrument 10 is broadly illustrated in FIG. 1. The instrument 10 includes a microwave instrument housing 11 typically made of rugged plastic. The housing 11 protects internal components described herein. The housing 11 is vented with slotted apertures 14 to facilitate cooling of the internal components. The instrument 10 includes a microwave cavity 19 and a vessel 20 for holding reactants, reaction solvent, products, and absorbent chromatography media. Further illustrated in FIG. 1 are communication devices for the instrument 10, specifically a keyboard 16 and display 17. The instrument 10 further includes at least one auxiliary port 12 for additional attachments, such as a pressure attachment or an evaporation attachment. Additional parts of the vessel 20 shown in FIG. 1 include an adaptor 26, a gas inlet tube 28, a gas outlet tube 29, and a fitting 33 to connect the tubes to peripheral devices explained herein.

Figure 2:
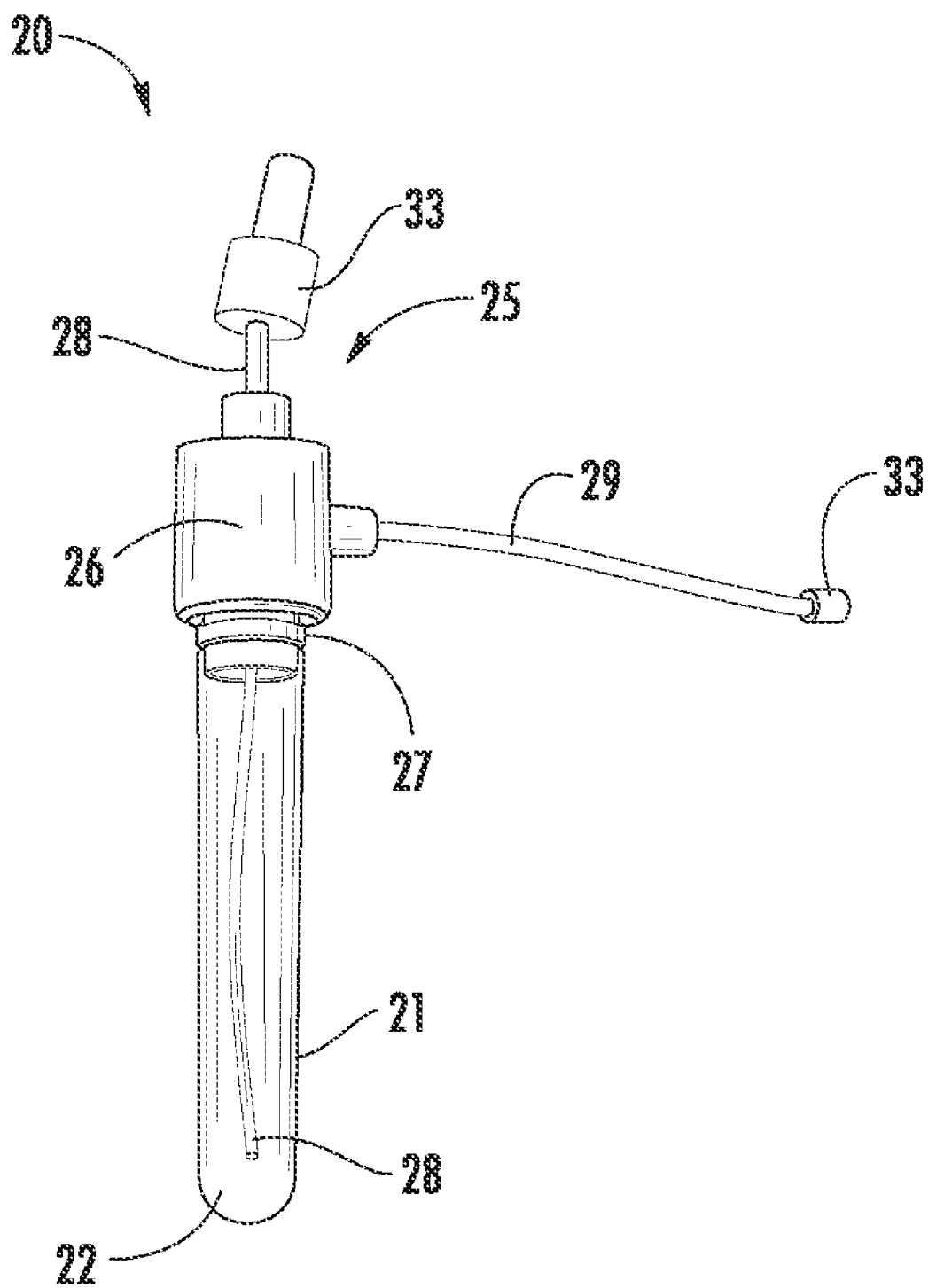
FIG. 2 is a perspective view of the vessel and its components.

FIG. 2 depicts the vessel 20 for holding reactants, reaction solvent, products, and absorbent chromatography media (i.e., compositions). The illustrated vessel 20 is a test tube shaped device having a wall 21 formed of a microwave transparent material defining an interior chamber 22 to hold the composition. The vessel is not, however, limited to specific vessel shapes and other vessel shapes (e.g., round-bottom flasks) can be incorporated as desired or necessary. The vessel 20 includes a top portion 25. The top portion 25 further includes an adaptor 26 having an O-ring 27 for connecting and sealing the adaptor 26 to the vessel wall 21. A hollow chemical resistant gas inlet tube 28 projects into the vessel 20, allowing gas to flow into the chamber 22. Similarly, a hollow chemical resistant vent tube 29 allows gas, particularly solvent vapor, to exit the chamber 22. In this manner, the gas inlet tube 28 and the gas outlet tube 29 allow make-up gas into the vessel 20 while allowing solvent to evacuate the vessel 20. The top portion 25 further includes a frit (not shown) for containing the composition within the vessel chamber 22 during gas flow. The frit is made of a chemical resistant media sufficiently porous to allow the flow of gas. The frit is disc-shaped having an opening to allow the gas inlet tube 28 to pass therethrough.

In preferred embodiments the interior chamber 22 has a volume of at least about 2.5 milliliters, which is a convenient size for bench-top experiments. It will be understood that the invention is not volume-limited, and that larger vessels can be used as may be necessary or desired. Suitable microwave transparent materials are well known to those of ordinary skill in the art, and include, for example, quartz, glass, and PYREX®.

The inlet tube 28 and the outlet tube 29 may have a fitting 33, generally denoted herein, for connecting the tube to another piece of equipment such as a vacuum pump (see FIG. 3) or gas reservoir. Appropriate fittings 33 are known to those of ordinary skill in the art and include, for example, threaded fittings, valves, quick-connect fittings, and hose clamps.

Figure 3:
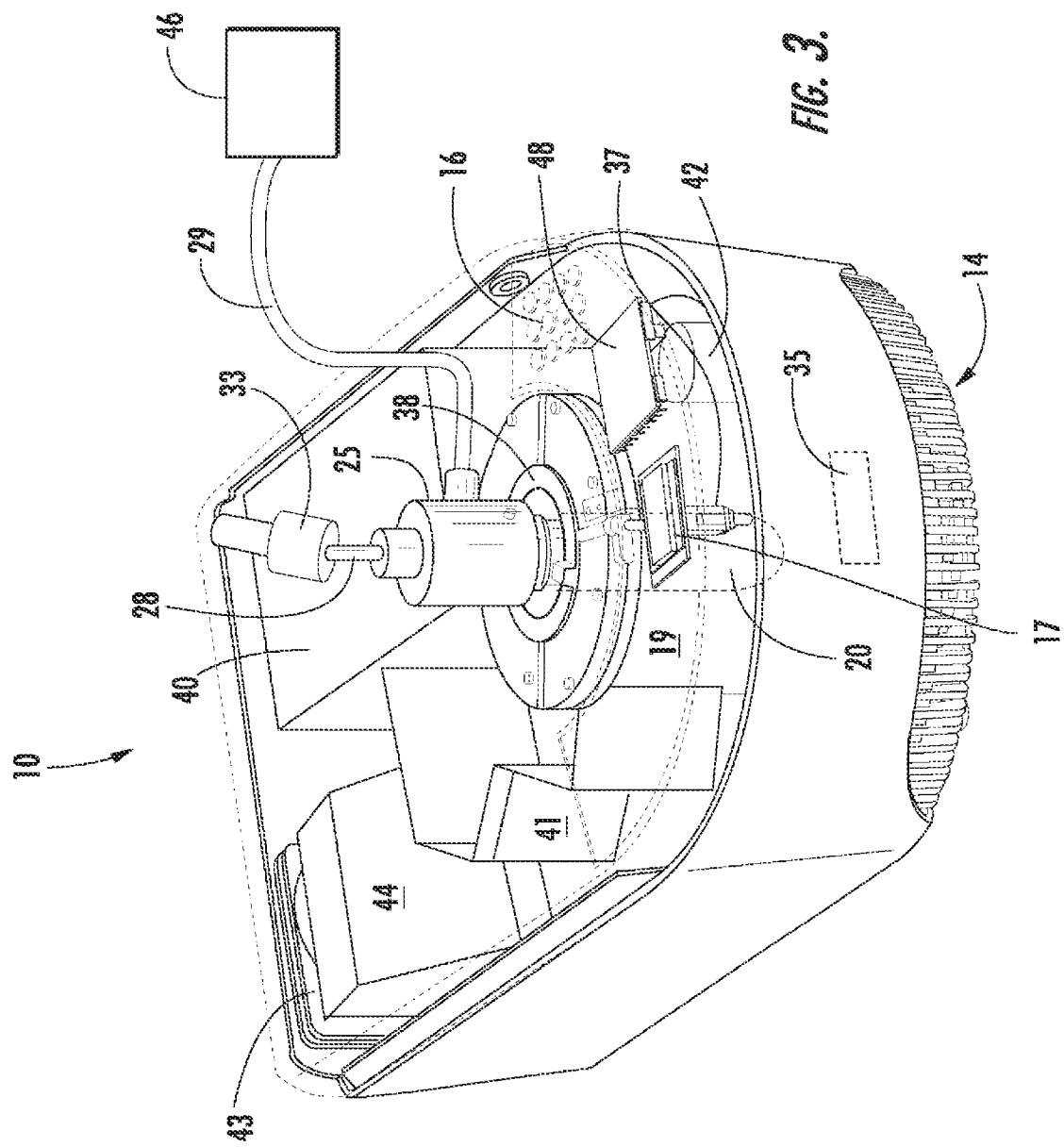
FIG. 3 is a cutaway diagram of the invention showing the instrument with the vessel placed in the microwave cavity.

FIGS. 1 and 3 show the microwave cavity 19 holding the vessel 20. In a preferred embodiment, the cavity 19 surrounds at least a portion of the vessel chamber 22. With respect to FIG. 3, the instrument's 10 various internal components are illustrated. FIG. 3 shows a microwave source 40, a waveguide 41, a stir motor 42, a fan 43 along with the fan housing 44, and various electronics.

A microwave source 40, as will be known to those of ordinary skill in the art, can be microwave generating devices such as magnetrons, klystrons, and solid state devices. Microwaves travel from the source 40 through the waveguide (schematically illustrated at 41) to the microwave cavity 19. The composition in the reaction vessel 20 absorbs the microwave energy as it enters the cavity 19. In this manner, the reaction cavity 19 is in microwave communication with the microwave source 40. In a preferred embodiment, the source 40 applies microwave energy to the reactants and the reaction solvent in the vessel 20 to accelerate the conversion of reactants to products.

Following product formation, an absorbent media (not shown) is mixed with the sample, typically by adding the media to the vessel 20 to absorb the reaction solvent and products. The absorbent media is preferably a chromatography media selected from the group consisting of silica, sand, alumina, and diatomaceous earth. Microwave energy is further applied to evaporate the reaction solvent. During the application of microwaves, a gas pump (schematically designated at 46) in gas communication with the vessel 20, preferably in communication with the gas exit tube 29, moves gases through the vessel 20 thereby facilitating the evaporation of reaction solvent from the chromatography media. In preferred embodiments, the gas pump 46 is a vacuum pump for pulling gases from the vessel and thereby reducing the gas pressure over the sample. Although a "hard" vacuum (e.g., approaching 0 Torr) is not required, the vacuum pump is a preferred device for reducing the pressure by the desired or necessary amount. In a preferred embodiment shown in FIG. 2, the gas inlet tube 28 includes a chemical resistant tube projecting into the vessel chamber 22 to carry make-up air near the bottom of the chromatography media inside to ensure thorough drying of the media. In this manner, the gas pump 46 maintains a vacuum in the vessel 20, specifically the vessel chamber 22, to facilitate the evaporation of the reaction solvent.

Alternatively, the gas pump 46 may be in physical communication with the gas inlet tube 28. In this arrangement, the pump 46 maintains pressure in the vessel 20, specifically the vessel chamber 22, to facilitate the evaporation of the reaction solvent from the chromatography media. In this embodiment, an inert gas is used to maintain the pressure in the chamber 22. Inert gas in this context refers to a gas that will not adversely react under the conditions in the vessel chamber 22. For example, a gas is chosen that will not ignite or otherwise combust with the composition in any given reaction state within the chamber 22. In many cases, inert gas can be selected from the group consisting of air, nitrogen, and argon. Alternatively, a pressurized gas reservoir (not shown) can replace the pump 46. In such cases a gas regulator (not shown) between the gas reservoir and the vessel 20 controls the flow of make-up gas.

The waveguide 41 is constructed of a material that reflects microwaves inward and prevents them from escaping in any undesired manner. Typically, such material is an appropriate metal which, other than its function for confining microwaves, can be selected on the basis of its cost, strength, formability, corrosion resistance, or any other desired or appropriate criteria. In preferred embodiments of the invention, the metal portions of the waveguide 41 and cavity are formed of stainless steel.

As is the case with other kinds of chemistry, it is advantageous in microwave assisted organic chemistry to stir and mix the composition in the vessel chamber 22. This is accomplished, for example, using a motor 42 to drive a magnetic stirrer, such as described in U.S. Patent Application Publication No. 20030170149, the contents of which are hereby entirely incorporated by reference.

The fan 43 serves to cool the electronics and the microwave source 40 portions of the instrument 10, as well as helping to keep the reaction cavity 39 from becoming overheated in the presence of ongoing chemical reactions. Other than having the capacity to appropriately cool the instrument and the cavity, the nature or selection of the fan 43 can be left to the individual discretion of those with skill in this art. In a typical embodiment, the fan 43 is mounted in a housing 44 to direct the flow of air across the electronics and the microwave source 40 to cool them more efficiently.

In a preferred embodiment, the instrument 10 includes a temperature sensor 35 and a pressure transducer 37 for measuring the temperature of the sample (i.e., composition) and for sensing the pressure inside the vessel 20, respectively. An appropriate temperature sensor can be selected from the group consisting of infra red detectors, ultraviolet detectors, and fiber optic sensors. In addition, the vessel top portion 25 is designed to withstand the increased pressure generated by some microwave assisted organic reactions. The vessel top portion 25 may include a pressure-resistant closure such as described in previously incorporated Publication No. 20030170149. In this embodiment, the vessel top portion 25 may be held in place on the cavity 19 with a retaining ring 38.

The instrument 10 includes a mechanism for adding chromatography media to the vessel 20 to absorb the reaction solvent and the products. The mechanism permits manually adding about an equal volume of chromatography media. Alternatively, the mechanism includes automatically adding about an equal volume of chromatography media.

FIG. 3 also shows the microprocessor 48. The electronics carried by the microprocessor 48 are generally well understood in their nature and operation. With respect to the present instrument, the microprocessor first controls the power from a given source, usually a wall outlet carrying standard current. The microprocessor also controls the operation of the device in terms of turning the microwave source 40 on or off, and in processing information received from the ongoing chemical reaction, in particular pressure and temperature. In turn, the processor is used to control the application of microwaves, including starting them, stopping them, or moderating them, in response to the pressure and temperature information received from the sensors previously described. The use of processors and related electronic circuits to control instruments based on selected measured parameters (e.g., temperature and pressure) is generally well understood in this and related arts. Exemplary (but not limiting) discussions include Dorf, *The Electrical Engineering Handbook, Second Ed.*, (1997) CRC Press LLC.

With respect to the instrument and method embodiments of the invention, the automated aspects of the instrument 10 are controlled by the microprocessor 48. This includes the control of simple peripheral devices such as the gas pump 46 and more complex devices including, but not limited to, CEM Corporation's EXPLORER™ and NAVIGATOR™ machines. See FIGS. 4 and 5. In a preferred embodiment, the invention is a modular device adapted to control peripheral devices while utilizing microwave energy to accelerate the process. Therefore, the preferred embodiment of the invention is simultaneous microprocessor control of the instrument 10, including the application of microwave energy, moderating the application of microwave energy based on the monitored temperature or pressure from the previously mentioned sensors, peripheral devices in electronic and physical communication with the instrument 10, and the respective methods incorporated by various combinations of the instrument 10 and peripheral devices.

In another aspect, the invention is a microwave assisted chromatography sample preparation instrument 10. Referring to FIG. 3, the instrument 10 includes a microwave source 40, a mechanism for controlling the application of microwave energy from the source 40, and a vessel 20 in wave communication with the source 40 for evaporating solvent.

The mechanism for controlling the application of microwave energy is the microprocessor 48. In one embodiment of the invention, controlling the application of microwave energy applies the energy in pulses to avoid overheating the sample in the vessel 20. An exemplary method for moderating the application of microwave energy is to incorporate a variable power supply such as disclosed in commonly assigned U.S. Pat. No. 6,084,226. Pulsing the microwave energy helps control the by-product of thermal heat. This decreases the likelihood of damaging or destroying the absorbent chromatography media and the reaction products absorbed therein.

The instrument is also useful if a vessel other than that depicted in FIG. 2 is used. For example, U.S. Pat. Application Publication No. 20030205456 to Jamalabadi et al., discloses a preloaded chromatography module (i.e., sample collector) having a plastic casing. The use of a reaction solvent with a high boiling point, such as dimethylsulfoxide (DMSO) or dimethylformamide (DMF), will require a large amount of microwave energy to evaporate the solvent. The heat generated during evaporation could melt the plastic casing and ruin the sample. The variable power supply mechanism discussed above solves this problem by controlling the input of energy while monitoring the temperature of the sample.

With respect to the previously described elements of the invention, the instrument 10 further includes a gas inlet tube 28 about the vessel 20 for allowing make-up gas into the vessel 20, a gas exit tube 29 about the vessel 20 for allowing solvent to evacuate the vessel 20, and a gas pump 46 in physical communication with the vessel 20 to facilitate the evaporation of solvent. In this embodiment, the gas pump 46, the gas inlet tube 28, and the gas exit tube create a gas flow through the vessel 20 to evaporate the solvent from the chromatography sample during and between applications of microwave energy.

The instrument 10 includes the advantage of the previously discussed integration of microprocessor control over other electronics and peripheral devices.

In another aspect, the invention is a method of preparing samples for column chromatography. The method includes the step of mixing a sample, including a reaction solvent, with a solid phase chromatography medium and applying microwave energy to the sample while concurrently providing a gas flow over and around the sample. The solvent is thereby encouraged to evaporate under the influence of the microwave energy and the flowing gas.

As previously discussed, the preferred embodiment of the method of the invention (and necessarily the instrument and peripherals that carry out the method) includes microprocessor control.

Figure 4:
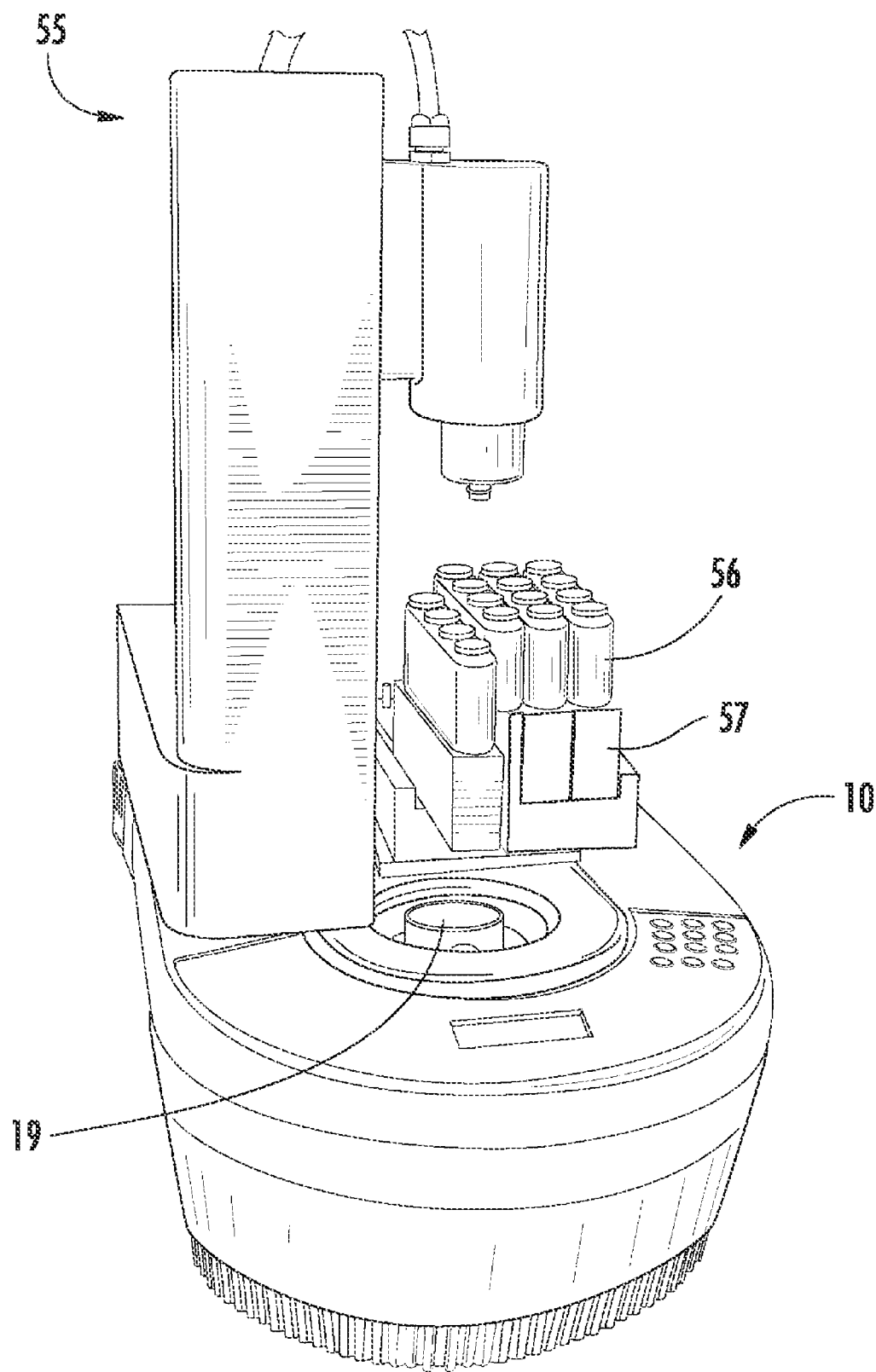
FIG. 4 is a perspective view of the invention with respect to a method embodiment of the invention.

An example is shown in FIG. 4. One embodiment of the method of the invention is carried out using the instrument 10 previously described with the EXPLORER™ peripheral attachment 55. The sample, including reaction solvent, is mixed with the chromatography medium in the sample collector 56. In this embodiment, the sample collector 56 is a single use chromatography module, typically a plastic cylindrical case pre-loaded with chromatography media. In this arrangement, the sample is added to the media already in the collector 56. Although different from the multi-use vessel 20 previously described, the method of the instant invention is adaptable for use of the sample collector 56 in appropriate sample holder racks 57. The EXPLORER™ attachment 55 lowers the sample collector 56 into the cavity 19 where the sample collector 56 is exposed to microwave energy. The instrument 10, in conjunction with a gas pump (not shown) concurrently provides a gas flow over and around the sample to evaporate the solvent as described.

The chromatography preparation method utilizes microprocessor control over the application of microwaves, gas flow, temperature monitoring (before, during, and after solvent evaporation), moderating microwave energy based upon the monitored temperature, and varying the microwave energy application time depending on the sample volume. The step of applying microwave energy to the sample while concurrently providing gas flow over and around the sample essentially dries the solvent from the chromatography media. The step of creating a gas flow further comprises creating a vacuum in the vessel. The method illustrated in FIG. 4 may be performed manually or preferably fully automated.

The method of preparing samples for column chromatography includes the field of chromatography known as flash chromatography. Flash chromatography is a simple, rapid form of preparative column liquid chromatography. Flash chromatography is useful for the rapid component separation of reaction products, for example, to test the percent completion of a given reaction under certain conditions, or to measure the amount of reactants converted to products under various experimental parameters.

The method includes applying microwave energy to a sample composition containing at least one solvent having reactants dissolved therein. The application of microwave energy encourages a chemical reaction and generates desired products. Thereafter, the microwave energy is turned off and an absorbent media is added to the sample to absorb the solvent. In a preferred embodiment, the media is compatible with the liquid chromatography that will subsequently separate the expected products. That is, the media is compatible with the solid and mobile phases used in the flash chromatography step to separate, identify, and purify the product components. The absorbent media is selected from the group consisting of silica, sand, alumina, and diatomaceous earth.

The absorbent media is mixed with the sample in an amount sufficient to provide a substantially dry mixture of the media and the sample, but less than an amount that overly broadens the resolution of the sample during liquid chromatography. For example, an insufficient amount of chromatography media added to the sample and exposed to microwave energy will result in a viscous mixture from which the reaction products cannot be easily separated. This tends to render the sample useless for further analysis. An excess amount of chromatography media added to the sample and exposed to microwave energy will negatively affect the resolution of the products in subsequent analysis. In a preferred embodiment, the volume of absorbent media used is about equal to the volume of solvent with products dissolved therein.

In this embodiment, the chromatography media can be added to the vessel containing the sample, thus avoiding the need to transfer the sample between vessels.

Thereafter, the microwave energy is applied to the dry mixture of the media and the sample to encourage the solvent to evaporate under the influence of the microwave energy. Next, the method includes adding the dry mixture of the media and the remaining sample to a liquid chromatography column and separating the components of the remaining sample for identification and purification purposes.

In this manner, the sample preparation method carries out the microwave assisted reaction in a microwave transparent vessel, mixes absorbent media with the sample in the same vessel to produce the dry mixture in the vessel, and applies microwave energy to the dry mixture to remove the solvent while the dry mixture remains in the same vessel.

In a preferred embodiment, the method is automated and controlled by a microprocessor. Furthermore, with the use of microwave energy for both product synthesis and evaporation of solvent from the chromatography media, the microprocessor controls a cooling fan to actively cool the sample and prevent overheating of internal components.

In another aspect, the invention is a method of preparing samples for column chromatography, including flash chromatography, and includes adding a scavenging composition to the sample to remove contaminants and excess reagents.

Scavenging compositions include, but are not limited to, electrophile scavengers, nucleophile scavengers, base scavengers, acid scavengers.

The method further includes adding a coupling reagent to the sample to facilitate the synthesis of products and adding a catalyst reagent to the sample to accelerate the rate of the reaction. These steps are left to the discretion of the researcher.

Scavengers, coupling reagents, and catalysts are known to one of ordinary skill in the art of organic chemical synthesis. In chemistry, a scavenger is defined as any substance added to a system or mixture to consume or inactivate traces of impurities (*Hawley's Condensed Chemical Dictionary, Twelfth Edition* (1993); Van Nostrand Reinhold). Extensive, but not limiting, lists of scavengers, coupling reagents, catalysts, and other reagents acceptable for use with the method of the invention are found in the Stratospheres™ Synthesis and Purification Guide published by Polymer Laboratories and the Organic Synthesis and Purification Catalog (2003-2004) published by Silicycle™. Some reagents mentioned in the catalogs are bound to a solid phase resin, such as silica, for convenience. It should be known, however, that the reagents do not need to be bound to a solid phase to be chemically active.

The method of the invention further includes accelerating the steps of scavenging, coupling, and catalyzing (collectively or individually) with microwave energy.

In yet another aspect, the invention is a method of dry-loading samples for column chromatography. The method includes adding an amount of chromatography media to a vessel holding a sample, the sample being dissolved in a solvent. The solvent is then evaporated using microwave energy, leaving dried chromatography media containing the sample. The dried chromatography media containing the sample is thereafter dry-loaded onto a separation chromatography column (such as a flash chromatography column) for identification and purification of the sample components.

The steps of adding chromatography media to the vessel, evaporating the solvent using microwave energy, and loading the dried chromatography media containing the sample onto a separation chromatography column are performed manually, or in a preferred embodiment, performed automatically.

Figure 5:
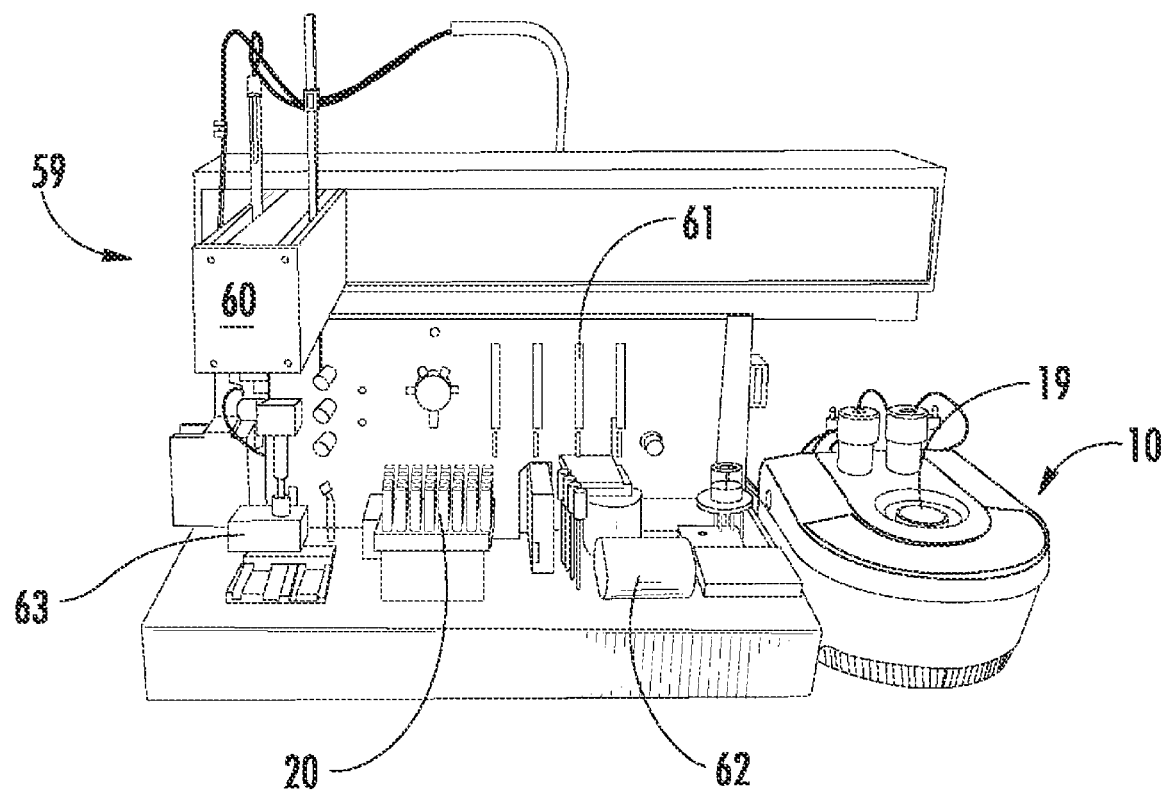
FIG. 5 is a further perspective view of the invention with respect to a method embodiment of the invention.

For example, and with respect to the instrument 10 of the invention, FIG. 5 depicts the instrument 10 with the NAVI- GATOR™ peripheral device 59 attached. The NAVIGATOR™ device 59 in combination with the instrument 10 of the present invention provides one embodiment of the method for automatic microwave assisted organic chemical synthesis and purification. The automated aspect of the NAVIGATOR™ 59 is typically aided by a robotic arm 60.

By way of example, the NAVIGATOR™ device 59 in combination with the instrument 10 of the present invention will begin chemical synthesis by placing liquid reactants dissolved in a reaction solvent from the liquid handling pumps 61 into the microwave transparent vessel 20. Coupling reagents, catalysts, and liquid scavenging compositions may also be added at this time. Next, the vessel top portion (not shown) is placed onto the vessel 20 at the capping/decapping station 62. The robotic arm 60 then moves the vessel 20 to the microwave cavity 19 of the instrument 10 where microwave energy encourages the conversion of reactants to products. Following product formation, the robotic arm 60 moves the vessel 20 to the capping/decapping station 62, and removes the vessel top portion. If necessary, a scavenging agent may be added at this time. If the scavenging agent is a liquid, the vessel 20 is placed under a liquid handling pump 61. If the scavenging composition is a solid (e.g., a scavenging molecule attached to a solid phase media), the vessel 20 is moved to the chromatography media reservoir 63. In a preferred embodiment, the scavenging composition is a solid as previously described and the media is an absorbent chromatography media selected from the group consisting of silica, sand, alumina, and diatomaceous earth. The vessel top portion is then replaced.

The step of scavenging to remove contaminants and excess reagents is accelerated by the application of microwave energy. Thus, the vessel 20 is moved back to the microwave cavity 19 for exposure to microwave energy. In some embodiments, the reaction solvent is concurrently evaporated, while in other embodiments microwave energy is applied to the scavenger-sample mixture before the sample is mixed with the chromatography media. Solvent evaporation is aided using one of the two previously discussed mechanisms for moving gas through the vessel, e.g., the gas pump (not shown) will maintain a vacuum in the vessel to facilitate the evacuation of solvent, or the gas pump or a gas reservoir (not shown) will maintain pressure in the vessel to facilitate the evacuation of solvent. Solvent evaporation leaves dried chromatography media containing the sample.

Following evaporation of the solvent from the dry mixture, the dried chromatography media is dry-loaded onto a separation chromatography column (not shown), such as a flash chromatography column, and the product components are separated for identification and purification purposes.

The method appreciates the same benefits of microprocessor control as previously described, such as automatic control of at least the steps of carrying out the reaction, applying microwave energy to the sample. The microprocessor may further "pulse" the microwave energy as previously described.

Figure 6:
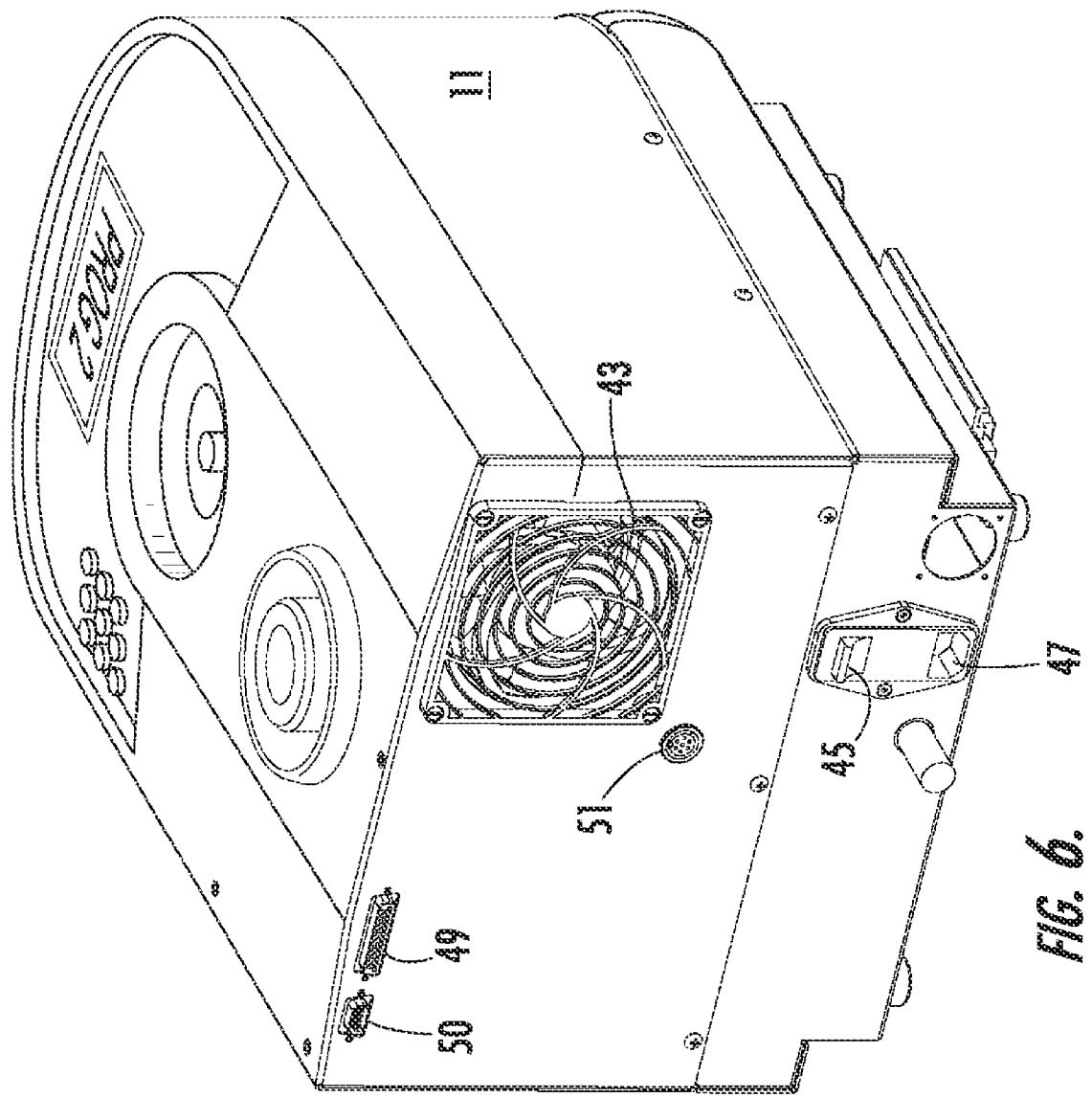
FIG. 6 is a perspective view of the invention showing the back of the instrument.

FIG. 6 is a rear perspective view of the instrument housing 11 that illustrates some additional items. FIG. 6 illustrates the cooling fan 43, a power switch 45, and a power cord inlet 47. In order to take advantage of the full capacity of the instrument, in preferred embodiments, the instrument includes a parallel port 49 and a serial port 50 for receiving input from or providing output to other electronic devices, particularly microprocessor based devices, such as the pump 46 (FIG. 3), personal computers, personal digital assistants or other appropriate devices (not shown). Similarly, FIG. 6 illustrates a connector 51 for the pressure transducer 37 previously described.

In the specification and the drawings, typical and preferred embodiments of the invention have been disclosed. Specific terms have been used only in a generic and descriptive sense, and not for purposes of limitation. The scope of the invention is set forth in the following claims.

The invention claimed is:

1. A method of preparing samples for column chromatography comprising:
    applying microwave energy to a sample composition containing at least one solvent to encourage a chemical reaction and generate desired products;
    thereafter mixing an absorbent media with the sample to absorb the solvent, the media being compatible with liquid chromatography that will separate the expected products, being chemically inert to the expected products, and being added in an amount sufficient to provide a substantially dry mixture of the media and the sample, but less than an amount that overly broadens the resolution of the sample during liquid chromatography;
    thereafter applying microwave energy to the dry mixture of the media and the sample to thereby encourage the solvent to evaporate under the influence of the microwave energy; and
    thereafter adding the dry mixture of the media and the remaining sample to a liquid chromatography column and separating the components of the remaining sample for identification and purification purposes.

2. A sample preparation method according to claim 1 comprising:
    carrying out the microwave assisted reaction in a microwave transparent vessel;
    mixing the absorbent media with the sample in the same vessel to produce the dry mixture in the vessel; and
    applying the microwave energy to the dry mixture to remove the solvent while the dry mixture remains in the same vessel.

3. The method as in claim 2 comprising computer microprocessor control of at least the steps of carrying out the reaction and applying microwave energy to the sample.

4. The method as in claim 3 wherein the step of carrying out a reaction comprises using pulsed microwave energy controlled by the microprocessor.

5. The method as in claim 1 wherein the sample is actively cooled using a cooling fan.

6. The method as in claim 1 wherein the absorbent media is selected from the group consisting of silica, sand, alumina, and diatomaceous earth.

7. The method as in claim 6 wherein the absorbent media comprises a volume of media about equal to the volume of solvent.

8. A method of preparing samples for column chromatography, comprising:
    applying microwave energy to a sample composition containing at least one solvent to encourage a chemical reaction and generate desired products;
    mixing a scavenging composition with the sample to remove contaminants and excess reagents;
    mixing an absorbent media with the sample to absorb the solvent, the media being compatible with liquid chromatography that will separate the expected products, being chemically inert to the expected products, and being added in an amount sufficient to provide a substantially dry mixture of the media and the sample, but less than an amount that overly broadens the resolution of the sample during liquid chromatography;

thereafter applying microwave energy to the dry mixture of the media and the sample to thereby encourage the solvent to evaporate under the influence of the microwave energy; and thereafter adding the dry mixture of the media and the remaining sample to a liquid chromatography column and separating the components of the remaining sample for identification and purification purposes.

9. The method of claim 8 wherein the step of adding a scavenging composition to the sample comprises electrophile scavenging compositions, nucleophile scavenging compositions, base scavenging compositions, and acid scavenging compositions.

10. The method of claim 8 further comprising the step of applying microwave energy to the scavenger-sample mixture to accelerate the scavenging removal of contaminants and excess reagents prior to the step of mixing the absorbent media with the sample.

11. The method of claim 8 comprising adding a coupling reagent to the sample to facilitate the conversion of reactants to products.

12. The method of claim 8 comprising adding a catalyst reagent to the sample to accelerate the rate of the reaction.

13. The method of claim 8 wherein column chromatography comprises the technique of flash chromatography.

14. A method of dry-loading samples for column chromatography, comprising:

adding an amount of chromatography media to a vessel holding a sample, the sample being dissolved in a solvent;

evaporating the solvent using microwave energy, leaving dried chromatography media containing the sample; and dry-loading the dried chromatography media containing the sample onto a separation chromatography column for identification and purification of the sample components.

15. The method according to claim 14 wherein the step of adding an amount of chromatography media to a vessel comprises an amount about equal to the amount of solvent.

16. The method according to claim 14 wherein the step of adding an amount of chromatography media to the vessel comprises manually adding the chromatography media to the vessel.

17. The method according to claim 14 wherein the step of loading the dried chromatography media containing the sample onto a separation chromatography column comprises manually loading the chromatography media onto the column.

18. The method according to claim 14 wherein the step of adding an amount of chromatography media to the vessel comprises a microprocessor in electronic control of adding an amount of chromatography media to the vessel.

19. The method according to claim 14 wherein the step of evaporating the solvent using microwave energy comprises a microprocessor in electronic control of the microwave energy.

20. The method according to claim 19 wherein the step of evaporating the solvent using microwave energy comprises a microprocessor in electronic control of pulsing the microwave energy.

21. The method according to claim 14 wherein the step of dry-loading the dried chromatography media containing the sample onto a separation chromatography column comprises a computer microprocessor in electronic control of loading the dried chromatography media containing the sample onto a separation chromatography column for identification and purification of the sample components.

* * * * *